United States Patent [19]

Reifschneider

[11] 4,424,217

[45] Jan. 3, 1984

[54] SUBSTITUTED PHENYL PHOSPHOROTHIOATES AND THEIR USE AS PESTICIDES

[75] Inventor: Walter Reifschneider, Walnut Creek, Calif.

[73] Assignee: The Dow Chemical Company, Midland, Mich.

[21] Appl. No.: 307,966

[22] Filed: Oct. 2, 1981

[51] Int. Cl.$^3$ .................. A01N 57/14; C07F 9/165
[52] U.S. Cl. ................................ 424/216; 260/949
[58] Field of Search .................. 260/949; 424/216

[56] References Cited

U.S. PATENT DOCUMENTS 3,042,703  7/1962  Schegk et al. ............... 260/949
3,351,682  11/1967  Baker et al. ................. 260/949
4,065,558  12/1977  Gordon ........................ 424/216

FOREIGN PATENT DOCUMENTS 1183494  12/1964  Fed. Rep. of Germany .

OTHER PUBLICATIONS

Anvarified Translation of Japanese Pat. No. 11880/66.

*Primary Examiner*—Anton H. Sutto
*Attorney, Agent, or Firm*—S. Preston Jones; Ronald G. Brookens

[57] ABSTRACT

O,O-Dialkyl O-[4-(tert-alkylsulfinyl)-2-chlorophenyl] phosphorothioate and the corresponding sulfonyl compounds are active insecticides for the kill and control of codling moth larvae.

15 Claims, No Drawings

SUBSTITUTED PHENYL PHOSPHOROTHIOATES AND THEIR USE AS PESTICIDES

BACKGROUND OF THE INVENTION

Many phosphate and phosphorothioate esters are known to have pesticidal activity of one kind or another. Various related sulfur-substituted phosphorothioate esters are also known to be active insecticides and miticides. A number of such esters are described in U.S. Pat. No. 3,042,703, West German Patent No. 1,183,494, and Japanese Patent No. 11880/66. These patents all disclose esters having the general structural formula

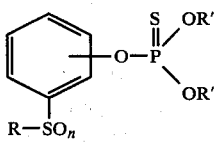

where the phenyl group may have one or more inert substituents, R' is a lower alkyl group, usually methyl or ethyl, R is also a lower alkyl group, and n is zero, one, or two. No compounds are shown where R is a tertiary alkyl group.

SUMMARY OF THE INVENTION

It has now been found that certain phosphorothioate esters generally described by the above formula where R is a tertiary butyl or tertiary amyl group have unexpectedly different insecticidal properties as compared to otherwise similar esters having a non-tertiary alkyl substituent. These new esters have the formula

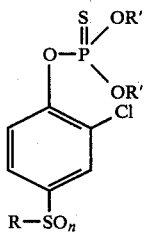

where R is a tertiary butyl or tertiary amyl group, R' is methyl or ethyl and n is one or two. These esters have been found to have particular activity as contact insecticides for the kill and control of codling moth larvae and the invention comprises the four defined compounds, insecticidal formulations containing one or more of those compounds, and the use of such formulations for killing and controlling coddling moth larvae.

DETAILED DESCRIPTION

The compounds of the present invention are useful as insecticides in a variety of household, industrial and agricultural operations, for the kill and control of codling moth larvae (*carpocapsa pomonella*).

When applied to plants, plant parts and their habitats to protect the plants from the attack of codling moth larvae, the subject compounds exhibit good residual control of the insect.

The method of the present invention comprises contacting the codling moth larvae with an insecticidally effective or inactivating amount of one, two, or all of the compounds of the present invention. The contacting can be effected by application of one or a combination of the compounds to the insect or its habitat, particularly fruit such as apples and pears. The inactivation can be lethal, immediately or with delay, or can be a sublethal one in which the inactivated insect is not able to carry out one or more of its normal like processes. This latter situation prevails when one of the systems of the insect, typically the nervous system, is seriously disturbed.

The inactivation of an insect by the application of an insecticidally effective or inactivating amount of one or a combination of these compounds is critical to the method of the present invention. These compounds can be employed in unmodified form, or modified by the addition of a pesticidal adjuvant thereto.

Compositions employing one or a combination of these active compounds can be in the form of a liquid or a dust; and the adjuvant employed can be any one of a plurality of materials including aromatic solvents, petroleum distillates, water, or other liquid carriers, propellent substances, surface-active dispersing agents, light absorbers, and finely divided carrier solids. In such compositions, the adjuvant cooperates with the phosphorus compound so as to obtain a composition to facilitate the method of the present invention, and to obtain an improved result. The use of either a surface-active dispersing agent and a finely divided carrier solid, simultaneously constitute preferred embodiments of the method of the present invention.

Another preferred embodiment of the present invention is a composition comprising one or a combination of the compounds, an organic liquid as a solvent and carrier therefor, and a propellant material. Numerous other embodiments will become available to those skilled in the art in view of the teachings set forth hereinbelow.

The exact concentration of one or a combination of the compounds of the present invention in a composition thereof with an adjuvant therefor can vary; it is only necessary that one or a combination of the compounds be present in a sufficient amount so as to make possible the application of an insecticidally effective or inactivating concentration. A preferred spray concentration is from about 25 to about 500 ppm. Generally, for practical applications, the active compound(s) can be broadly applied to codling moth larvae or their habitat in compositions containing from about 0.00001 to about 98 percent by weight of the phosphorus compound(s).

In the preparation of dust compositions, one or a combination of these phosphorus compounds can be compounded with any of the finely divided carrier solids such as pyrophyllite, diatomaceous earth, gypsum and the like. In such operations, the finely divided carrier is ground or mixed with the compound(s), as active agent(s) or wetted with a solution of the active agent(s) in a volatile organic solvent. Similarly, dust compositions containing the phosphorus product(s) can be compounded with various solid dispersing agents, such as fuller's earth, attapulgite and other clays. These dust compositions can be employed as treating compositions or can be employed as concentrates and subsequently diluted with additional solid dispersing agent or with pyrophyllite, diatomaceous earth, gypsum and the like to obtain the desired amount of active agent in a treating composition. Also, such dust compositions can be dispersed in water, with or without the aid of surfactant, to form spray mixtures.

Furthermore, a compound, a combination of the compounds or a dust concentrate composition containing such compound(s) can be incorporated in intimate mixture with surface-active dispersing agents such as ionic and nonionic emulsifying agents to form spray concentrates. Such concentrates are readily dispersible in liquid carriers to form sprays containing the toxicant(s) in any desired amount. The choice of dispersing agent and amount thereof employed are determined by the ability of the agent to facilitate the dispersion of the concentrate in the liquid carrier to produce the desired spray composition.

In the preparation of liquid compositions, the product or a combination of the products can be compounded with a suitable water-immiscible organic liquid and surface active dispersing agent to produce an emulsifiable liquid concentrate which can be further diluted with water and oil to form spray mixtures in the form of oil-in-water emulsions. In such compositions, the carrier comprises an aqueous emulsion, that is, a mixture of water-immiscible solvent, emulsifying agent and water. Preferred dispersing agents to be employed in these compositions are oil-soluble and include the nonionic emulsifiers such as polyoxyethylene derivatives or sorbitan esters, complex ether alcohols and the like. However, oil-soluble ionic emulsifying agents such as mahogany soaps can also be used. Suitable organic liquids to be employed in the compositions include petroleum oils and distillates, toluene, liquid halohydrocarbons and synthetic organic oils.

When operating in accordance with the present invention, one of the products, a combination of products or a composition containing one or more of the products is applied to the codling moth larvae to be controlled directly, or by means of application to their habitat in any convenient manner, for example, by means of hand dusters or sprayers. Application to fruit trees is conveniently carried out with power dusters, boom sprayers and fog sprayers. In such foliar applications, the compositions to be employed should not contain any appreciable amounts of any phytotoxic diluents. In large-scale operations, dusts or low volume sprays can be applied from an airplane. The present invention also comprehends the employment of compositions comprising one or a combination of these phosphorus compounds, an adjuvant, and one or more biologically active materials, such as other insecticides, fungicides, miticides, bactericides, nematocides, and the like.

The phenolic intermediates for making the compounds of this invention are readily prepared from known compounds by conventional means. A preferred method comprises reacting 2-chloro-4-mercaptophenol with tertiary butyl alcohol or tertiary amyl alcohol at about 50°–100° C. in inert solvent solution in the presence of sulfuric or phosphoric acid to produce the 4-(t-alkylthio)-2-chlorophenol. That product is readily isolated by adding water to the reaction mixture and separating the product from the organic layer thereby formed by conventional means.

This 4-(t-alkylthio)-2-chlorophenol can then be oxidized to the corresponding sulfinyl phenol by reacting it with about a stoichiometric equivalent of any convenient oxidizing agent under mild oxidizing reaction conditions. Suitable oxidizing agents include nitric acid, hydrogen peroxide, and benzoyl peroxide. A mode of oxidation using chlorine water to convert alkylthioaromatics to corresponding alkylsulfinyl compounds is described in U.S. Pat. No. 3,415,832. In the above oxidizing methods, an excess of the oxidizing agent and usually longer reaction times can be used to make the corresponding alkylsulfonyl phenols.

A more convenient method comprises the use of 30% $H_2O_2$ to oxidize the alkylthiophenol in glacial acetic acid at reflux temperature, using an equivalent amount of the hydrogen peroxide to make the alkylsulfinylphenol and a 50–75% excess of the theoretically required two moles of peroxide to make the alkylsulfonylphenol.

The O,O-diethyl phosphorochloridothioate intermediate reacted with the phenolic reactant to make the esters of this invention is a commercially available material.

EXAMPLE 1

O,O-Diethyl O-[4-(t-butylsulfinyl)-2-chlorophenyl]phosphorothioate

To a stirred mixture of 23.25 grams (0.1 mole) of 4-t-butylsulfinyl-2-chlorophenol, 15.9 grams of powdered anhydrous potassium carbonate and 200 milliliters of acetonitrile was added 18.9 grams (0.1 mole) of O,O-diethyl phosphorochloridothioate. The mixture was heated at 50°–55° C. with stirring for 4 hours. The insoluble salts formed during the reaction were removed by filtration under reduced pressure and the solvent was evaporated from the filtrate under reduced pressure. The liquid which remained as a residue was dissolved in methylene chloride and the resulting solution washed with water and dried over anhydrous sodium sulfate. The solvent was removed by evaporation under reduced pressure yielding 32.4 grams (84.3 percent of theoretical) of a yellow liquid. The O,O-diethyl O-[4-(t-butylsulfinyl)-2-chlorophenyl]phosphorothioate product thus recovered, had a refractive index at 25° C.=1.5425. The identity of the product was confirmed by NMR and elemental analyses.

EXAMPLE 2

O,O-Diethyl O-[4-(t-butylsulfonyl)-2-chlorophenyl]phosphorothioate

To a stirred mixture of 24.85 grams (0.1 mole) of 4-t-butylsulfonyl-2-chlorophenol, 15.9 grams of powdered anhydrous potassium carbonate and 200 milliliters of acetonitrile was added 18.9 grams (0.1 mole) of O,O-diethyl phosphorochloridothioate. The mixture was heated at 50°–55° C. for 4 hours with stirring. The mixture was cooled and the insoluble salts, formed during the reaction were removed by filtration and the solvent was then removed by evaporation under reduced pressure. The solid which remained as a residue was taken up in chloroform and recrystallized by adding hexane to obtain two crops of crystals, (1) 33.9 grams with a melting point of 95°–96.5° C. and (2) 1.7 grams with a melting point of 90°–93° C. The second crop was discarded leaving 33.9 grams of a white crystalline solid (85 percent of theoretical). The identity of this compound was confirmed as O,O-diethyl O-[4-(t-butylsulfonyl)-2-chlorophenyl]phosphorothioate by NMR and elemental analyses.

The tertiary-amyl-substituted compounds corresponding to the above two products were prepared by substituting equivalent quantities of 4-(t-amylsulfinyl)-2- chlorophenol and 4-(t-amylsulfonyl)-2-chlorophenol for the tertiary-butyl-substituted phenol intermediates in the procedures of Examples 1 and 2. Both of these products were obtained in essentially quantitative yields as viscous yellow oils. O,O-Diethyl O-[4-(t-amylsulfinyl)-2-chlorophenyl]phosphorothioate had a refractive index of 1.5428 at 25° C. while O,O-diethyl O-[4-(t-amylsulfonyl)-2-chlorophenyl]phosphorothioate had a refractive index of 1.5270 at the same temperature. Identities of these products were confirmed analytically as before.

EXAMPLE 3

The compounds set forth hereinbelow were dissolved in predetermined amounts of acetone and these mixtures were dispersed in predetermined amounts of water containing a small amount of a dispersing agent to prepare aqueous dispersions of varying concentrations with one of the phosphorus compounds as sole active toxicant. A dispersion was applied to sheets containing egg masses of the codling moth and to apple or pear fruit. After treatment, the egg sheets were attached to the treated fruit and the samples were incubated eight to ten days under conditions conducive to the hatching and growth of the larvae. Counts of larvae in the treated fruit were compared to those of the untreated check to determine percent control as is shown in Table 1. Also listed are the results obtained with the n-butyl sulfinyl and sulfonyl chlorophenyl esters corresponding to the tertiary alkyl substituted compounds of the invention.

TABLE 1

| Compound | Concentration in ppm of Active Compound | Percent and Control of codling Moth Larvae |
| --- | --- | --- |
| O,O—diethyl O—[4-(t-butylsulfinyl)-2-chlorophenyl]phosphorothioate | 400<br>200 | 100<br>80 |
| O,O—diethyl O—[4-(t-butylsulfonyl)-2-chlorophenyl]phosphorothioate | 400<br>100<br>25 | 95<br>90<br>75 |
| O,O—diethyl O—[4-(t-amylsulfinyl)-2-chlorophenyl]phosphorothioate | 500<br>100<br>25 | 100<br>90<br>80 |
| O,O—diethyl O—[4-(t-amylsulfonyl)-2-chlorophenyl]phosphorothioate | 500 | 80 |
| O,O—diethyl O—[4-(n-butylsulfinyl)-2-chlorophenyl]phosphorothioate | 400 | 0 |
| O,O—diethyl O—[4-(n-butylsulfonyl)-2-chlorophenyl]phosphorothioate | 400 | 0 |

The compounds of this invention have other useful insecticidal properties. For example, they are particularly effective against mosquito larvae, providing complete kill and control when applied in concentrations as low as 0.1 ppm.

I claim:

1. A method for killing and controlling codling moth larvae which comprises contacting said larvae or their habitat with a composition containing, as an active ingredient, an insecticidally effective amount of at least one compound of the formula

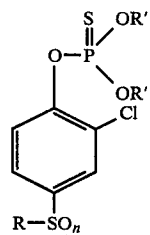

wherein R is a tertiary butyl or tertiary amyl group, R' is methyl or ethyl and n is an integer from one to two in intimate admixture with an inert carrier therefor.

2. The method of claim 1 wherein the active ingredient is O,O-diethyl O-[4-(t-butylsulfinyl)-2-chlorophenyl]phosphorothioate.

3. The method of claim 1 wherein the active ingredient is O,O-diethyl O-[4-(t-amylsulfinyl)-2-chlorophenyl]phosphorothioate.

4. The method of claim 1 wherein the active ingredient is O,O-diethyl O-[4-(t-butylsulfonyl)-2-chlorophenyl]phosphorothioate.

5. The method of claim 1 wherein the active ingredient is O,O-diethyl O-[4-(t-amylsulfinyl)-2-chlorophenyl]phosphorothioate.

6. The compound having the structural formula

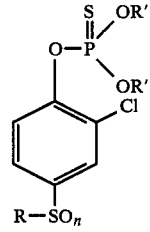

wherein R is a tertiary butyl or tertiary amyl group, R' is methyl or ethyl and n is an integer from one to two.

7. The compound of claim 6 wherein R is a tertiary butyl group, n is one, and the compound is O,O-diethyl O-[4-(t-butylsulfinyl)-2-chlorophenyl]phosphorothioate.

8. The compound of claim 6 wherein R is a tertiary amyl group, n is one, and the compound is O,O-diethyl O-[4-(t-amylsulfinyl)-2-chlorophenyl]phosphorothioate.

9. The compound of claim 6 wherein R is a tertiary butyl group, n is two, and the compound is O,O-diethyl O-[4-(t-butylsulfonyl)-2-chlorophenyl]phosphorothioate.

10. The compound of claim 6 wherein R is a tertiary amyl group, n is two, and the compound is O,O-diethyl O-[4-(t-amylsulfinyl)-2-chlorophenyl]phosphorothioate.

11. An insecticidal composition comprising, as an active ingredient, an insecticidally effective amount of at least one compound of the formula

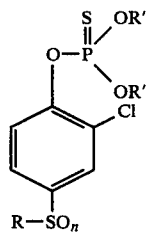

wherein R is a tertiary butyl or tertiary amyl group, R' is methyl or ethyl and n is an integer from one to two in intimate admixture with an inert carrier therefor.

12. The composition of claim 11 wherein the active ingredient is O,O-diethyl O-[4-(t-butylsulfinyl)-2-chlorophenyl]phosphorothioate.

13. The composition of claim 11 wherein the active ingredient is O,O-diethyl O-[4-(t-amylsulfinyl)-2-chlorophenyl]phosphorothioate.

14. The composition of claim 11 wherein the active ingredient is O,O-diethyl O-[4-(t-butylsulfonyl)-2-chlorophenyl]phosphorothioate.

15. The composition of claim 11 wherein the active ingredient is O,O-diethyl O-[4-(t-amylsulfinyl)-2-chlorophenyl]phosphorothioate.

* * * * *